United States Patent
Kawabata et al.

(10) Patent No.: US 6,424,418 B2
(45) Date of Patent: *Jul. 23, 2002

(54) SURFACE PLASMON RESONANCE SENSOR APPARATUS USING SURFACE EMITTING LASER

(75) Inventors: Yuji Kawabata, Isehara; Tadashi Okamoto, Yokohama; Hajime Sakata, Atsugi; Masanori Sakuranaga, Atsugi; Tsuyoshi Nomoto, Atsugi, all of (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/318,761

(22) Filed: May 26, 1999

(30) Foreign Application Priority Data

May 29, 1998 (JP) .......................................... 10-165998

(51) Int. Cl.⁷ ............................................... G01N 21/55
(52) U.S. Cl. ...................................................... 356/445
(58) Field of Search .................................. 356/448, 445

(56) References Cited

U.S. PATENT DOCUMENTS

| | | | | | |
|---|---|---|---|---|---|
| 5,508,809 | A | * | 4/1996 | Peacock et al. | 356/445 |
| 5,898,503 | A | * | 4/1999 | Keller et al. | 356/445 |
| 5,917,607 | A | * | 6/1999 | Naya | 356/445 |

FOREIGN PATENT DOCUMENTS

| EP | 0282009 | 9/1988 |
|---|---|---|
| JP | 292045 | 12/1986 |
| JP | 018890 | 1/1993 |
| JP | 167192 | 7/1993 |
| JP | 058873 | 3/1994 |
| JP | 167443 | 6/1994 |
| JP | 237043 | 8/1994 |
| JP | 265336 | 9/1994 |
| JP | 174693 | 7/1995 |
| JP | 225185 | 8/1995 |

OTHER PUBLICATIONS

Millot; et al. "A Reactive . . . resonance". Sens and Act. B29 (1995) 268–273.
Kunz, et al., "Sensing . . . devices", Sens. and Act. B32 (1996) 149–155.
Niggemann, et al.; "Remote Sensing . . . Spectroscopy"; Sens. and Act. B34 (1996) 328–333.
Melendez, et al.; "A commercial . . . Plasmon sensing"; Sens. and Act. 35–36 (1996) 212–216.
Ha yashi, et al.; "Record . . . Structure"; Elec. Ltrs., 31 7 (1995) 560–562.
Babic, et al. "Double–Fused . . . Lasers"; Appl. Phys. Lett. 66, (9) Feb. 1995, 1030–1032.
Watanabe et al. "Observation of Adsorbates by Surface–Enhanced Spectroscopy" vol. 20, No. 6 (1982), 289–304.
Specht et al., "N–terminal variants . . . E. Coli", J. Biotech, vol. 33 (1994), 259–269.

* cited by examiner

Primary Examiner—Richard A. Rosenberger
(74) Attorney, Agent, or Firm—Fitzpatrick, Cella, Harper & Scinto

(57) ABSTRACT

A surface plasmon resonance sensor apparatus includes a common substrate, a surface emitting laser, such as a VCSEL, arranged on the common substrate, a sensor array, such as CCD array, arranged on the common substrate, a light-transmitting medium provided above the common substrate, and a metal thin film formed on the light-transmitting medium to cause surface plasmon resonance due to light which is emitted from the surface emitting laser, transmitted through the light-transmitting medium and impinging on the metal thin film. The surface emitting laser, metal thin film and sensor array are positioned such that a change in an intensity of light reflected by the metal thin film caused by the surface plasmon resonance can be measured by the sensor array.

25 Claims, 6 Drawing Sheets

SURFACE PLASMON RESONANCE SENSOR APPARATUS USING SURFACE EMITTING LASER

BACKGROUND OF THE INVENTION

1. Field of the Invention

The present invention relates to a sensor apparatus for measuring an object in a sample using light. More particularly it relates to a sensor apparatus for detecting or measuring a specific substance by using the interaction between light and a surface plasmon wave caused by the total-reflection of light on a metal thin film provided on a light-transmitting medium. The typical sensor apparatus is a nucleic-acid detecting device, in which a vertical cavity surface emitting laser (VCSEL) and a sensor array, such as an array of charge-coupled devices (CCDs), are arranged on a common substrate, and an optical system composed of integrally formed substrate, light-transmitting medium and metal thin film is employed.

2. Related Background Art

Conventionally, oxidation-reduction reaction of a measurement object, color reaction of a measurement object with color reagent, and the like have been used in chemical sensors for measuring sample concentrations. In those cases, when a highly-sensitive, highly-selective sensor is needed, it is preferable that the measurement object is used as a substrate and a biosubstance with a strong affinity for the substrate, such as an antibody for an antigen, is used for the substrate. Where the measurement object is nucleic acid, then a so-called probe nucleic acid can be preferably used. In this probe nucleic acid, a portion of a base arrangement in the nucleic acid is replaced by a complementary base arrangement.

Recently, a highly-sensitive method has been proposed to optically measure a change in the dielectric constant which accompanies a biochemical reaction (see Japanese Patent Application Laid-Open No. 61(1986)-292045). In this method, the interaction between light and surface plasmon wave is used. The surface plasmon wave is generated under a total-reflection condition of light on a metal thin film provided on a light-transmitting medium. Its principle of measurement is as follows.

Figure 6:
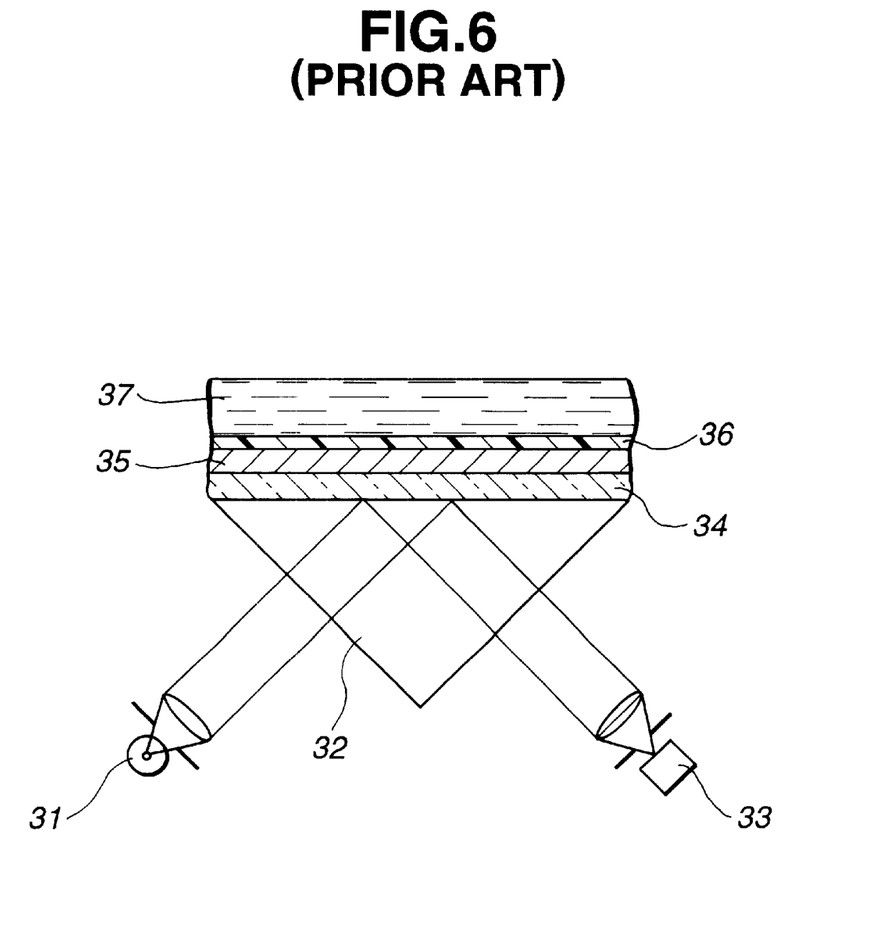
FIG. 6 is a schematic cross-sectional view illustrating a prior art measuring apparatus.

FIG. 6 illustrates the structure of the above-discussed prior art measuring apparatus. In FIG. 6, light emerging from a light source 31 enters a prism 32 (a light-transmitting medium), is reflected at a reflective surface of the prism 32, and is detected by a photodetector 33. A spacer layer 34 of a buffer medium, a metal film 35 and an organic material layer 36 (an insulator) are serially desposited on the reflective surface of the prism 32. A sample fluid 37 of a measurement object is in contact with an external surface of the organic material layer 36.

A surface plasmon wave is defined herein as an electromagnetic wave generated at the interface between a metal and an insulator. This wave can be optically induced when the resonance condition determined by refractive index (i.e., dielectric constant) in the vicinity of the interface between the metal and the insulator and its thickness is satisfied. Initially, p-polarized light is caused to impinge on the light-transmitting medium with the metal thin film thereon such that a total reflection of the light occurs at the metal thin film. Then, an evanescent wave occurs with a wave number depending on the incident angle of light at the interface between the metal thin film and the light-transmitting medium. On the other hand, the surface plasmon wave is generated on an outer surface (a surface in contact with the insulator) of the metal thin film due to a tunneling effect of light. The surface plasmon resonance occurs when wave numbers of the evanescent wave and the surface plasmon wave respectively created on both faces of the metal thin film are coincident with each other. At this time, part of energy of the incident light is used to induce energy of the surface plasmon wave.

The intensity of light reflected at the metal thin film is equal to a difference between the intensity of the incident light and the light intensity lost by the excitation of the surface plasmon wave, based on the energy conservation law. Therefore, the surface plasmon resonance can be measured by measuring the incident-angle dependency of the intensity of the reflected light. The resonance condition is determined from the wavelength of incident light, its incident angle, complex dielectric constants of light-transmitting medium and metal thin film, complex dielectric constant of a sensor's sensitive film provided on the metal thin film, and so forth. When the complex dielectric constant varies due to the biochemical reaction in the sensitive film, the resonance condition is changed. Hence, under the condition of a constant wavelength, the light incident angle for causing the surface plasmon resonance is varied. When this variation of the light incident angle is detected, the substrate concentration of the biochemical reaction, i.e., concentration of the measurement object, can be obtained.

Since the surface plasmon wave is generated in a region within about several hundred nanometers on the metal thin film, the biochemical reaction between substrate and biosubstance causing the change in the dielectric constant must be effected in this region. Therefore, a very thin film will suffice to form the sensitive film with the biosubstance fixed thereon. Further, only the neighborhood of the metal thin film can be measured in the surface plasmon resonance, so even a colored sample and a suspended sample can be measured without the influences of the color or suspension.

Hitherto, a detecting sensor of an antigen of protein, and the like have been developed using the surface plasmon resonance (for example, BIAcore by Phalmasia Co.). In this sensor, an organic thin film as the sensitive film is provided on the metal film on which the surface plasmon resonance occurs, and an antibody is fixed in the organic thin film. When the fixed antibody is selectively bonded to the antigen in the measurement object, the dielectric constant of the organic thin film is slightly changed. This change can be measured from a change in the resonant angle. This principle can also be used in a nucleic-acid sensor and the like, in which an organic thin film as the sensitive film is provided on the metal film on which the surface plasmon resonance occurs, and a nucleic acid or the like is fixed in the organic thin film. When the fixed target nucleic acid or probe nucleic acid is selectively bonded to probe nucleic acid or target nucleic acid in the measurement object, the dielectric constant of the organic thin film is slightly changed and this change can be measured from a change in the resonant angle.

Such a measuring apparatus using the surface plasmon resonance is disclosed in Japanese Patent Application Laid-Open Nos. 5(1993)-18890, 6(1994)-58873, 6(1994)-167443, 6(1994)-265336, 7(1995)-174693, "Sensors and Actuators B329 (1995) pp. 268–273", or "Sensors and Actuators B32 (1996) pp. 149–155", for example. In those apparatuses, a metal thin film is formed on a prism, and the surface plasmon resonance created by incidence light from outside of the prism is measured by a detector disposed on the outside of the prism. In those apparatuses, the incident angle of light incident on the metal thin film needs to be varied to measure a change in the resonant angle. Hence, the apparatus becomes relatively large including light source, prism, detector, movable device, and so forth. Accordingly, a sensor apparatus with a large elasticity is difficult to fabricate based on such a construction.

Further, the metal thin film for creating the surface plasmon resonance can achieve a sufficiently exact measurement with a very small area. Therefore, there have also been proposed sensor-type apparatuses in which only the measuring portion is shaped into a minute configuration. For example, "Sensors and Actuators B34 (1996) pp. 328–333" proposed a sensor using an optical fiber. Since the group velocity of light propagated through an optical fiber is determined from its wavelength, incident and reflection angles of light totally reflected at the interface between the core and the cladding of the fiber are dependent on the wavelength of light and characteristics of the fiber.

Here, a portion of the cladding in the optical fiber is removed, and a metal thin film is deposited on the surface of the cladded portion. When the resonance occurs between an evanescent wave generated during the total reflection at the interface between core and metal thin film and a surface plasmon wave on the metal thin film at a resonant wavelength of various wavelengths, light at its resonant wavelength attenuates. Therefore, when white light is inputted into the optical fiber and the wavelength dispersion of light transmitted through the core and the metal thin film is detected, the attenuation of the light intensity in a wavelength range of the surface plasmon resonance can be measured. Those methods drastically increase a practicable potential of the sensor using the surface plasmon resonance. Those methods, however, require a strict optical positioning of the coupling between light source and optical fiber, the coupling between optical fiber and optical detector, and so forth.

A similar sensing technique using the optical fiber is further disclosed in Published European Patent Application No. 0282009. This technique is directed to an optical fiber sensor using a change in refractive index resulting from the interaction with hydrocarbons. The operating principle is based on a change in the refractive index of the cladded material caused by the presence of hydrocarbon.

Further, there has been proposed a device which includes no driving unit for changing the incident angle of light and in which a prism and an optical detector are integrally arranged. Japanese Patent Application Laid-Open No. 7(1995)-225185 discloses a sensor apparatus in which light waveguide, waveguide-type lens and CCD detector are arranged on a glass substrate, for example. Light from a semiconductor laser is inputted into this sensor, and the surface plasmon resonance is measured. The sensor is advantageous in that a relative positional relation between respective optical elements need not be adjusted after the fabrication of the sensor.

Furthermore, "Sensors and Actuators B35–36 (1996) pp. 212–216" proposes a sensor apparatus in which a light emitting diode and a photodiode array are integrally arranged. In this sensor apparatus, all optical elements needed for the surface plasmon resonance measurement are packed in a single package, and a sensitive film is deposited on a metal thin film formed on the package to achieve the function of the sensor apparatus. In the sensor apparatus, a wide width of the incident angle of light incident on the metal thin film is obtained by using a wide expansion of light emitting from the light emitting diode, and the light intensity corresponding to each incident angle can be detected by the photodiode array. The sensor apparatus needs no adjustment of the optical arrangement for measurement of the surface plasmon resonance, and the sensor's function is established by fixing biosubstance to the metal thin film. In this sensor apparatus, however, a sensor is needed for each measurement object, and the sensor apparatus is hence unsuitable for many-component sensing.

As described above, the chemical sensor using the surface plasmon resonance measures the change in the intensity of reflected light during the total reflection which depends on the incident angle. Accordingly, for the purpose of highly-precise measurement, an appropriate relative position between light source, p-polarizer, lens, light-transmitting medium and photodetector must be strictly established. Further, in the method for measuring the reflected light while changing the incident angle of light, respective optical elements must be moved with a high positional precision. To dispose those optical elements, highly-rigid material must be used to fix them, precision is required to mount and drive them, and the size of the apparatus inevitably increases since control systems for driving and so forth must be used.

Further, in the method for measuring the surface plasmon resonance at the core portion of the optical fiber, a versatile sensor can be obtained with high elasticity. However, problems occur in that: couplings of light source and photodetector to the optical fiber are needed; a reference portion is needed to cope with external influeneces of temperature and so forth; a sensor portion is needed for each measurement object in a many-component simultaneous measurement; and a large number of spectroscopes and photodetectors are needed because of the measurement of the surface plasmon resonance using wavelength dispersion. Thus, productivity and versatility of the sensor are reduced.

On the other hand, in the surface plasmon resonance sensor apparatus provided with an integrated arrangement of light source, polarizer, photodetector and light-transmitting medium, no strict positioning of the optical elements is needed and no driving unit is needed. Accordingly, it is possible with this integrated arrangement to achieve a small sensor size and stability in sensor response. However, when a light emitting diode is used as the light source, since light emerging from a radiation point of the diode expands in a conical form, only a single-component measurement can be performed even when the above-discussed photodiode array is used. Since, however, a variety of components are typically present in a sample, there is a great unfulfilled need for their simultaneous measurement. Further, where the concentration of the measurement object in the sample ranges broadly, development of a sensor apparatus with a large dynamic range is also desired.

SUMMARY OF THE INVENTION

It is an object of the present invention to provide a surface plasmon resonance sensor apparatus in which a surface emitting laser employed as a light source and superior in light directivity, controllability of its polarization plane and suitability for arraying, and a sensor array, such as a CCD array, are arranged on a common substrate, wherein a many-component measurement can be readily performed as well as a single-component measurement by using a light-transmitting medium and a metal thin film provided above the substrate, such that dynamic range can be readily widened.

The objects and advantages of the present invention are achieved by:

A surface plasmon resonance sensor apparatus which comprises:

(a) a common substrate;

(b) a sensor array spaced on said common substrate;

(c) a light-transmitting medium spaced above said common substrate;

(d) a metal thin film formed on said light-transmitting medium; and (e) a surface emitting laser spaced on said common substrate adapted to emit light through said light-transmitting medium to be reflected from said metal thin film and simultaneously generate a surface plasmon resonance sufficient to change intensity of light reflected from said metal thin film; wherein said surface emitting laser, said metal thin film and said sensor array are positioned to measure the intensity of the light reflected by the metal thin film.

More specifically, a surface plasmon resonance sensor apparatus includes a common substrate, a surface emitting laser, such as a vertical cavity surface emitting laser (VCSEL), arranged on the common substrate, a sensor array, such as a CCD array, arranged on the common substrate, a light-transmitting medium provided above the common substrate, and a metal thin film formed on the light-transmitting medium. When light is emitted from the surface emitting laser is transmitted through the light-transmitting medium and impinges on the metal thin film, a surface plasmon resonance is induced. The surface emitting laser, metal thin film and sensor array are positioned such that the change in intensity of light reflected by the metal thin film, which is caused by the surface plasmon resonance can be measured by the sensor array.

More specifically, the following preferred embodiments may be employed based on the above fundamental invention.

DESCRIPTION OF THE PREFERRED EMBODIMENTS

The surface emitting laser and the sensor array are arranged on the common substrate. An optical element is provided above the laser to expand a divergent angle of the light emitted from the surface emitting laser. This optical element can be omitted, if desired. The light-transmitting medium provided with the metal thin film is provided above the substrate. The light-transmitting medium is preferably a resin case filled with air. On an internal surface of the resin case an antireflection film may be formed, and on an external surface, the metal thin film is provided. The respective elements are positioned such that the laser light can be totally reflected at the metal thin film and the light intensity along a direction of the light divergent angle can be measured by the sensor array.

Metal forming the metal thin film is preferably Ag, Au, Cu, Zn, Al or K, as is described in "SURFACE, Vol. 20 No. 6 (1982) pp. 289–304". Ag and Au are particularly preferable. The metal thin film can also be composed of an alloy composition, but an alloy mixing Pd with Au is not good since the surface plasmon disappears when Pd is mixed with Au. Further, the metal thin film can be comprised of, for example, a multi-layer structure in which a very thin film of Cr is formed on the surface of the light-transmitting medium and an Au film or the like is formed on the Cr film to secure a tight contact between the metal thin film and the light-transmitting medium.

As employed herein, the term "thin" in the phrase "metal thin film" refers to a metal film thickness sufficient to totally reflect the light striking it from the light transmitting medium. In general, the thickness of the metal film is from about 100 to 1000 Å, preferably from about 300 to 700 Å and most preferably about 500 Å for most metals. A "very thin" film is generally from about 300 to 500 Å in thickness.

In a specific sensor apparatus, the light radiation point of the surface emitting laser is elliptically shaped. The laser is positioned such that light from the laser enters the metal thin film as p-polarized light. A lens or a hologram device is preferably provided to expand the light beam along its polarization plane, and the total reflection of the light occurs at the metal thin film over a wide incident-angle range. The dependency of the thus-effected surface plasmon resonance on the incident angle is measured by the sensor array, such as a one-dimensional CCD sensor array arranged extending along the above polarization plane on the common substrate.

The number of CCDs in the one-dimensional CCD sensor array is determined by the range of the incident angle of light received by the CCD sensor array and the variation of the surface plasmon resonant angle. Over a hundred (100) CCDs will usually suffice for that purpose, when the incident-angle range is about 10° and the resonant-angle variation is about 2°. Further, where a hologram device is used to expand the laser beam, the beam expansion angle can be freely set by a thin, light element and the above-discussed optical positioning above the surface emitting laser can be readily performed.

In another specific sensor apparatus, a one-dimensional array of parallel-arranged surface emitting lasers and a two-dimensional sensor array are arranged on the common substrate. Light from the surface emitting laser is preferably further expanded in a direction of its polarization plane by the lens or hologram device. However, light beams from adjacently-arranged lasers seldom overlap in a direction perpendicular to the polarization plane since the expansion angle of the laser light in this perpendicular direction is exceedingly small. Thus, undesired crosstalk seldom occurs in the two-dimensional sensor array. Therefore, many components or items can be simultaneously measured when different biosubstances are respectively fixed to different strip portions of the metal thin film on which surface plasmon resonances occur due to the light beams from the respective lasers. Further, when the same biosubstance is fixed to the different strip portions at different concentrations, the sensor construction, in which respective dynamic ranges are varied, can be obtained.

In another specific sensor apparatus, a two-dimensional array of surface emitting lasers and a two-dimensional sensor array are arranged on the common substrate. Light beams from the surface emitting lasers arranged along the direction of the p-polarization plane are preferably transmitted by lenses or hologram devices to enter the interface between the light-transmitting medium and the metal thin film over appropriately-set incident-angle ranges, respectively. When the respective laser incident-angle ranges are continuously set by lenses or hologram devices, a wide incident-angle range, which could not be obtained by a single surface emitting laser, can be covered by the plural lasers. The intensity distribution of totally-reflected light corresponding to this wide incident angle is measured by the sensor array.

Where the complex dielectric constant of the sensitive film fixed to the metal thin film cannot be estimated, the resonant angle causing the surface plasmon resonance cannot be calculated and it is hence difficult to design the apparatus by using a sensor having only a narrow incident-angle range. In such a case, a sensor with a wide incident-angle range is very useful since it can measure the surface plasmon resonance for a wide dielectric constant of the sensitive dielectric film. Further, similarly to the case where the sensor apparatus includes the one-dimensional laser array, when different biosubstances are fixed to the strip portions of the metal thin film, many components or a single component can be measured with a large dynamic range by using a wide incident angle.

When the incident angle of the laser light on the metal thin film covers a large range, the intensity of light to be measured decreases since the radiation angle of light to be received by each sensor element varies broadly. In such a case, an accurate spectrum of the surface plasmon resonance can be obtained when signals detected by sensors, such as CCDs, are corrected.

The sensitive dielectric film to be used in the present invention is formed of a substance which selectively interacts with the measurement object and changes its physicochemical properties, such as its refractive index, thickness and the like. Specifically, the sensitive dielectric film is preferably a polymer film carrying antigen, antibody or the like, a Langmuir-Blodgett film, a polymer film carrying a substance such as a hormone, receptor, polypeptide, nucleic acid, cell, cell membrane, glycoprotein, lipid and pigment, which show an affinity for a specific organic compound, or the like. The measurement object may be a fluid, such as a gas or liquid.

Further, a preferred sensitive dielectric film to be used in the present invention selectively interacts with a nucleic acid to be measured and changes its physicochemical properties, such as its refractive index, thickness and the like. Specifically, a preferred sensitive dielectric film carries probe nucleic acid in which a portion of a base arrangement of a target nucleic acid to be measured is replaced by a complementary base arrangement. More specifically, the sensitive dielectric film contains DNA, RNA, PNA, or the like to act as a probe. In this case, the target nucleic acid is a reaction object. Conversely, the sensitive dielectric film may contain a target nucleic acid. More specifically, the sensitive dielectric film may contain DNA, such as cDNA, or RNA, such as mRNA, tRNA and rRNA. In this case, the probe nucleic acid is a reaction object.

In the thus-fabricated surface plasmon resonance sensor apparatus, the surface emitting laser and the sensor, such as CCD array, are formed on the common substrate and the metal thin film is formed on the light-transmitting medium, such as a resin, provided above the substrate. Thus, all optical elements needed to measure the surface plasmon resonance are disposed on a single chip. Therefore, small-sizing, cost-reduction and excellent productivity of the sensor apparatus can be readily attained. Further, even simultaneous sensing of many components can be achieved by using parallel characteristic (i.e., good directivity) of light emitted from the surface emitting laser and establishing a multi-channel construction. Further, since the surface emitting laser can be readily constructed as an array, a wide incident angle onto the sensor can be attained by combining the arrayed lasers with the sensor array. A many-component sensing sensor apparatus and a sensor apparatus applicable over a wide concentration range can also be achieved.

Features of the surface emitting laser will be described with reference to a typical specific structure.

Figure 1:
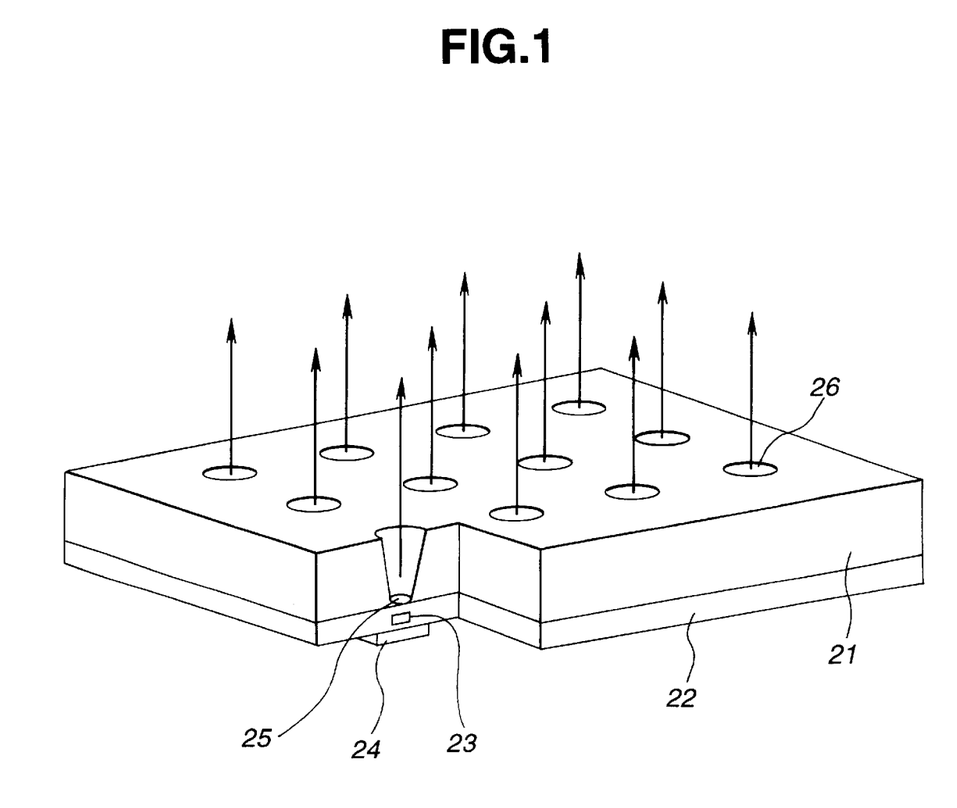
FIG. 1 is a partly cut-away perspective view illustrating a typical array structure of surface emitting lasers.

Surface emitting lasers in a range from blue of about 400 nm to a communication wavelength band of 1.55 $\mu$m have been presently developed. They have been studied using a GaN-series on a sapphire substrate, GaAlInP-series, InGaAs-series, GaInNAs-series and GaAlAs-series on a GaAs substrate, GaInAsP-series and GaAlInAs-series on an InP substrate, and other materials. A fundamental structure of a surface emitting laser array is illustrated in FIG. 1.

An epitaxially-grown layer structure 22 with a thickness of about several microns is fabricated on a semiconductor substrate 21, and an active layer 23 is provided in the layer structure 22. Dielectric multi-layer mirrors 24 and 25 with a high reflection factor of over 99% are formed on both surfaces of the layer structure 22. A pixel 26 shows a peripheral shape of the active layer 23, and laser light is emitted perpendicularly to the substrate 21. The reflective layers 24 and 25 are typically formed of multiple layers with a thickness of $\lambda/4$ and different refractive indices, and materials thereof are generally dielectric glasses or epitaxially-grown semiconductors. Examples of the epitaxially-grown mirror are disclosed in "ELECTRONICS LETTERS, 31, p. 560 (1995)", wherein AlAs/GaAs multi-layer mirror, active layer and so forth are deposited on an GaAs substrate during a single growth. As is disclosed in "APPLIED PHYSICS LETTERS, 66, p. 1030 (1995)", a GaAs/AlAs mirror formed on a GaAs substrate is bonded to a laser structure of InGaAsP/InP series grown on an InP substrate, using direct junction. Further, as is disclosed in Japanese Patent Application Laid-Open Nos. 5(1993)-167192 and 6(1994)-237043, the reflective mirror can also be fabricated by epitaxially growing it on a substrate with a hole.

The size of a light emitting portion of the laser device is in a range from 5 $\mu$m to 30 $\mu$m, and its beam expansion angle is exceedingly small (i.e., its directivity is excellent), compared with those of gas lasers and ordinary semiconductor lasers. Further, light emerging from the laser device can be polarized without using a polarizer, by elliptically shaping the light radiation point of the laser. Moreover, an array of multiple surface emitting lasers can be relatively readily fabricated on a single silicon substrate by using processing techniques.

On the other hand, it is well known that the sensor or photodetector, such as CCD, can be arranged in a one-dimensional or two-dimensional array.

These advantages and others will be more readily understood in connection with the following detailed description of the more preferred embodiments in conjunction with the drawings.

The following Examples represent preferred embodiments.

EXAMPLE 1

Figure 2A:
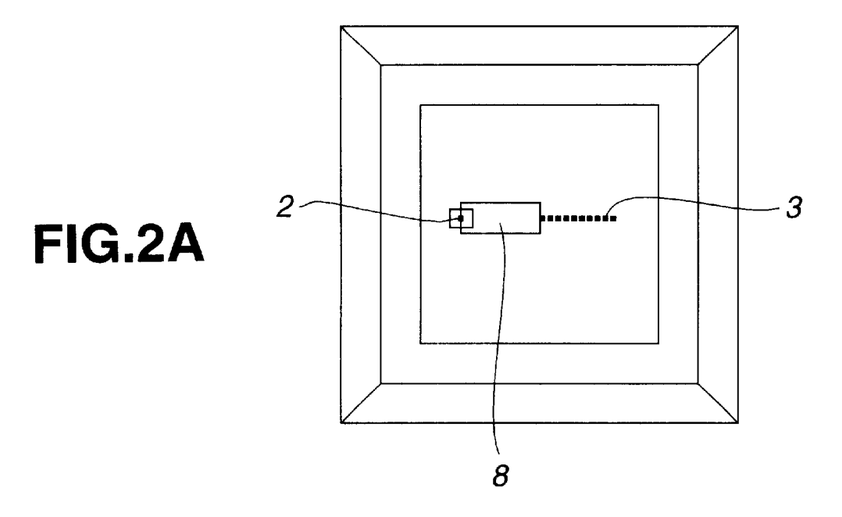
FIG. 2A is a plan view illustrating a first embodiment of a surface plasmon resonance sensor apparatus in which a surface emitting laser and a one-dimensional array of CCD sensors are arranged on a common substrate.
Figure 2B:
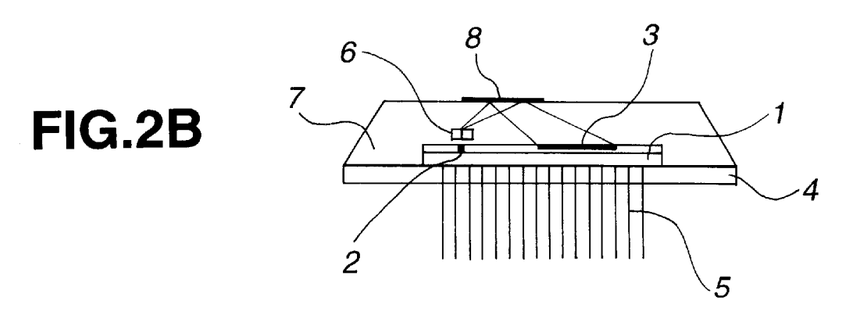
FIG. 2B is a side view illustrating the first embodiment of the surface plasmon resonance sensor apparatus.
Figure 2C:
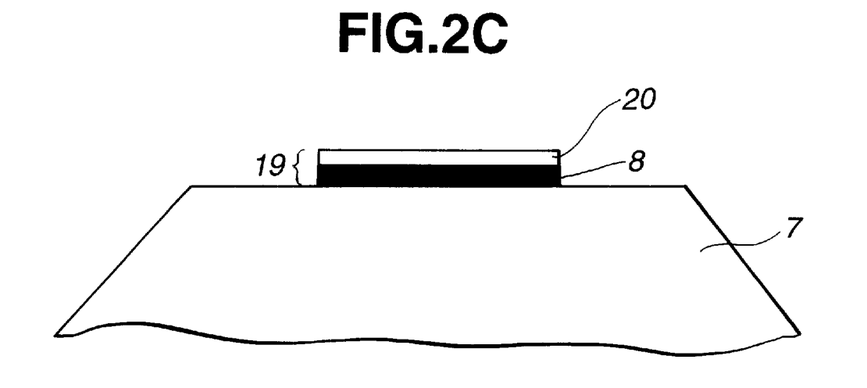
FIG. 2C is a side view illustrating the first embodiment with a sensitive dielectric layer.

A first preferred embodiment of the present invention is directed to a surface plasmon resonance sensor apparatus using a surface emitting laser and a one-dimensional CCD sensor array. Plan and side views of the sensor structure are illustrated in FIGS. 2A and 2B, respectively. FIG. 2C is a side view illustrating the first embodiment with a sensitive dielectric layer.

As illustrated in FIGS. 2A and 2B, the surface emitting laser 2 and the one-dimensional CCD sensor array 3 are arranged on a Si substrate 1 along a line extending in right and left directions of FIGS. 2A and 2B. The oscillation wavelength of the surface emitting laser 2 is 640 nm, and its output power is 0.1 mW. The Si substrate 1 may be put in a package with a window to maintain its mechanical strength. The Si substrate 1 may also be supported by an insulating substrate 4 as shown in FIG. 2B. Terminals 5 are drawn from the package or insulating substrate 4 to drive the surface emitting laser 2 and take out signals of the CCD sensor array 3. Further, since the dielectric constant (i.e., refractive index) exibits temperature dependence, it is preferable that a temperature sensor, such as a thermistor, is provided on or near the Si substrate 1. The temperature correction of the surface plasmon resonance signal is thus performed by taking out a signal from the temperature sensor through the terminal 5. Although the light from the surface emitting laser is polarized in a uniaxial direction, it is still preferable that a radiation point of the laser 2 is elliptically shaped or the polarization plane of light from the laser 2 is controlled by a polarizer or the like such that its polarization plane can be accurately aligned to the arrangement direction of the CCD sensor array 3.

A cylindrical lens 6 is provided above the surface emitting laser 1 to expand the laser light in the arrangement direction of the CCD sensor array 3. These elements are molded with a light-transmitting polymethylmethacrylate resin 7 to construct a sensor apparatus. The expanded laser light is totally reflected by an outer surface of a metal thin film 8. The focal length of the cylindrical lens 6 is set such that the intensity of the totally-reflected light can be measured by the CCD sensor array 3 corresponding to its incident angle. When the sensor array 3 is widely arranged and the totally-reflected light is thus received sufficiently accurately, the position of the cylindrical lens 6 is not needed to be so strictly set in the resin 7. As the metal thin film 8, gold is deposited to a thickness of 500 Å on the surface of the light-transmitting resin 7.

Anti-HIV-1 emv gp 120/160 monoclonal antibody is carried on the metal thin film 8 in the following manner to form a sensitive dielectric layer 19 as illustrated in FIG. 2C.

(1) Cystamine-2-hydrochloric acid salt (produced by Tokyo Kasei Kogyo Co.) is dissolved in chloroform to obtain a 0.005 M solution. The gold film 8 formed on the resin-mold surface of the sensor apparatus is dipped in this solution and maintained therein for three hours to introduce amino-residue on the gold thin film 8.

(2) BS3 [Bis (sulfosuccinimidyl) suberate] (produced by PIERCE Co.) is dissolved in 20 mM sodium phosphate buffer (pH 7.5) including 0.15 M NaCl to obtain 2 mM solution. The gold thin film 8 with the amino-residue introduced therein is dipped in this solution for ten minutes to introduce succinimidyl-residue on the gold thin film 8.

(3) Anti-HIV-1 emv gp 120/160 monoclonal antibody (produced by Bioline Co.) is then dissolved in 20 mM sodium phosphate buffer (pH 7.5) including 0.15 M NaCl to obtain a concentration of 1 mg/ml. The gold thin film 8 is dipped in this solution for an hour to carry the anti-HIV-1 emv gp 120/160 monoclonal antibody 20 on the gold thin film 8.

(4) The gold thin film 8 is finally dipped in 1 M Tris-HCl buffer (pH 7.5) for ten minutes, and unaltered succinimidyl-residue on the gold thin film 8 is caused to react.

The thus-completed sensor apparatus is dipped in 20 mM sodium phosphate buffer (pH 7.5) including 0.15 M NaCl. Light reflected by the gold thin film 8 is detected by the CCD sensor array 3, and its signals are taken out through the terminals 5. The output signals are observed by a synchroscope, and the surface plasmon resonance corresponding to each incident angle is measured. As a result, a resonance spectrum with a minimum at the incident angle of 62.0° was obtained as illustrated by a thick dotted line in FIG. 3A.

Antigen substance of recombinant HIV-1 gp 120 (produced by Repligen Co.), which is a detection-object material, is dissolved in buffer to obtain 0.02 mg/ml. The sensor apparatus is dipped in this antigen-substance solution, and the resonance spectrum is similarly measured. A resonance spectrum with a minimum at the incident angle of 64.0° was thus obtained as illustrated by a thin dotted line in FIG. 3A. It is thus apparent therefrom that the surface plasmon resonance sensor apparatus of the present invention is applicable to the detection of antigen-antibody reaction.

EXAMPLE 2

Next, as a second Example, probe DNA is carried on the metal thin film 8 in the following manner to form a sensitive dielectric layer.

(1) Cystamine-2-hydrochloric acid salt (produced by Tokyo Kasei Kogyo Co.) is dissolved in chloroform to obtain a 0.005 M solution. The gold film 8 formed on the resin-mold surface of the sensor apparatus is dipped in this solution and maintained therein for three hours to introduce amino-residue on the gold thin film 8.

(2) BS3 [Bis (sulfosuccinimidyl) suberate] (produced by PIERCE Co.) is then dissolved in 20 mM sodium phosphate buffer (pH 7.5) including 0.15 M NaCl to achieve a 2 mM solution. The gold thin film 8 with the amino-residue introduced therein is dipped in this solution for ten minutes to introduce succinimidyl-residue on the gold thin film 8.

(3) As the DNA probe, oligomer ① with a polymerization degree of 18, in which amino-residue is bonded to hydroxyl group at 5' terminal through phosphate group and hexamethylene, is used. As DNA, HPLC purified grade (produced by Nihon Seifun Co.) is used (also the same in the following embodiments). A base arrangement of the probe has an array complementary with a base arrangement in a portion of multiple cloning site in M13mp18ss of single-chain DNA. The base arrangement and linkage structure of each probe are as follows:

Further, DNA ② with a base arrangement complementary with ① is used as detection-object DNA.

The ① is dissolved in 20 mM sodium phosphate buffer (pH 7.5) including 0.15 M NaCl to achieve a concentration of 0.5 mg/ml. The gold thin film 8 is dipped in this solution for an hour to bond the probe DNA on the gold thin film 8.

(4) The gold thin film 8 is finally dipped in 1 M Tris-HCl buffer (pH 7.5) for ten minutes, and unaltered succinimidyl-residue on the gold thin film 8 is caused to react.

The thus-completed sensor is dipped in 20 mM sodium phosphate buffer (pH 7.5) including 0.15 M NaCl. Light reflected from the gold thin film 8 is detected by the CCD sensor array 3, and its signals are taken out through the terminals 5. The output signals are observed by a synchroscope, and the surface plasmon resonance corresponding to each incident angle is measured. As a result, a resonance spectrum with a minimum at the incident angle of 58.0° was obtained as illustrated by a thin dotted line in FIG. 3B.

The detection-object material of ② is then dissolved in buffer to achieve 0.005 mg/ml. The sensor apparatus is dipped in this solution, and the resonance spectrum is similarly measured. A resonance spectrum with a minimum at the incident angle of 58.7° was obtained as illustrated by a thick dotted line in FIG. 3B. It is thus apparent therefrom that the surface plasmon resonance sensor apparatus of the present invention is applicable to the detection of nucleic acid oligomer.

Figure 4A:
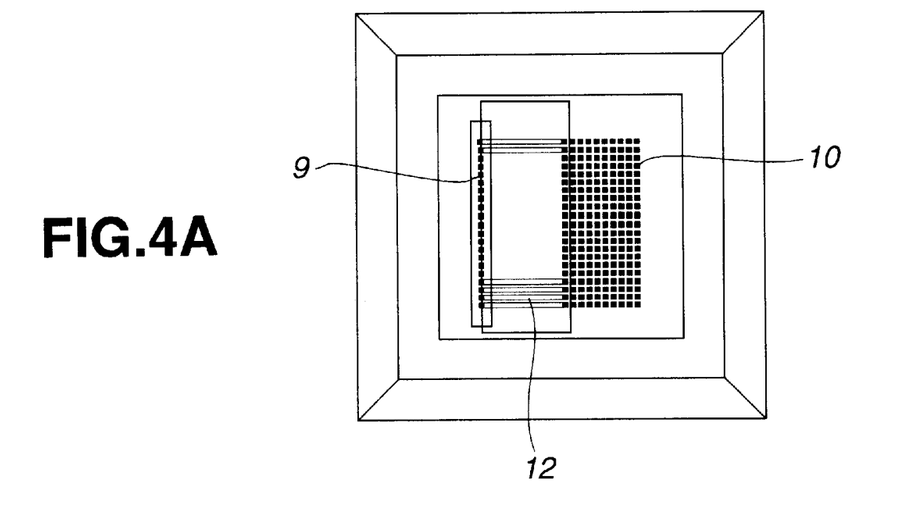
FIG. 4A is a plan view illustrating second and third embodiments of a surface plasmon resonance sensor apparatus in which a one-dimensional array of surface emitting lasers and a two-dimensional array of CCD sensors are arranged on a common substrate.
Figure 4B:
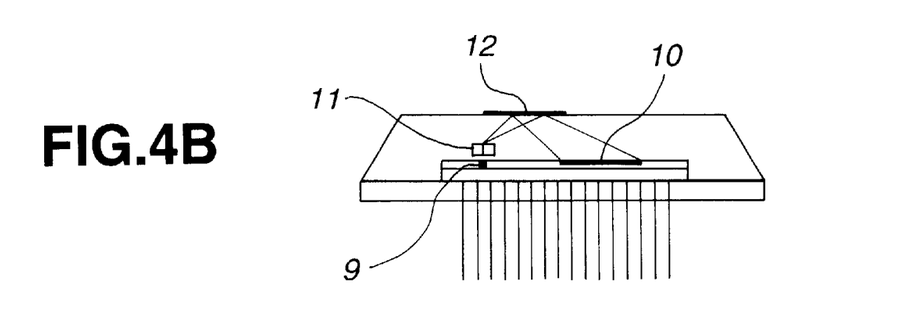
FIG. 4B is a side view illustrating the second and third embodiments of the surface plasmon resonance sensor apparatus.

A second preferred embodiment of the present invention is directed to a surface plasmon resonance sensor apparatus using a one-dimensional array of surface emitting lasers and a two-dimensional array of CCD sensors and capable of measuring many components simultaneously. Plan and side views of the sensor structure of this embodiment are illustrated in FIGS. 4A and 4B, respectively. As illustrated in FIGS. 4A and 4B, similarly to the first embodiment, the one-dimensional surface emitting laser array 9 and the two-dimensional CCD sensor array 10 are arranged on a Si substrate.

EXAMPLE 3

A cylindrical lens 11, which can be formed by extending the cylindrical lens 6 of the first embodiment in up and down directions in FIG. 4A, is provided above the surface emitting laser array 9 to expand each laser light emitted from each laser in the arrangement direction of each one-dimensional CCD sensor array of the two-dimensional CCD sensor array 10 for each laser (in right and left directions in FIGS. 4A and 4B). Each expanded laser light is totally reflected by the surface of light-transmitting resin on which a metal thin film 12 is formed. The focal length of the cylindrical lens 9 is set such that the intensity of each totally-reflected light can be measured by the CCD sensor array 10 corresponding to its incident angle.

As the metal thin film 12, gold is deposited with a thickness of 500 Å on the surface of the light-transmitting resin, similarly to the first embodiment. The vacuum evaporation area of the gold thin film 12 is sufficiently wide such that each laser light can be reflected by the surface of the gold film 12 and each surface plasmon resonance can be measured by each one-dimensional CCD sensor array extending in the right and left directions in the two-dimensional CCD sensor array 10.

Figure 3A:
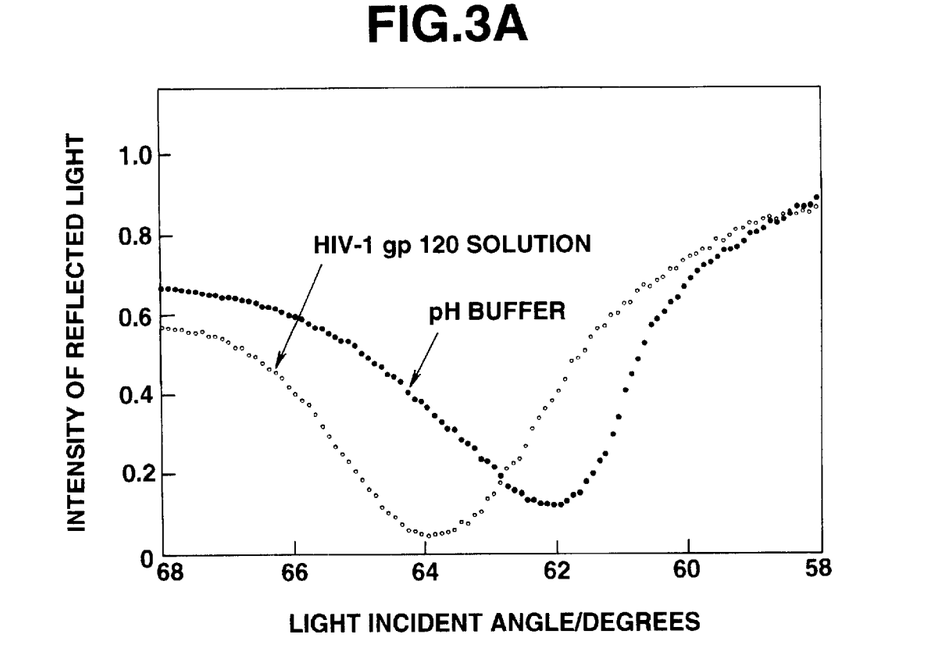
FIG. 3A is a graph illustrating resonance spectra obtained in respective cases in embodiments of the present invention.
Figure 3B:
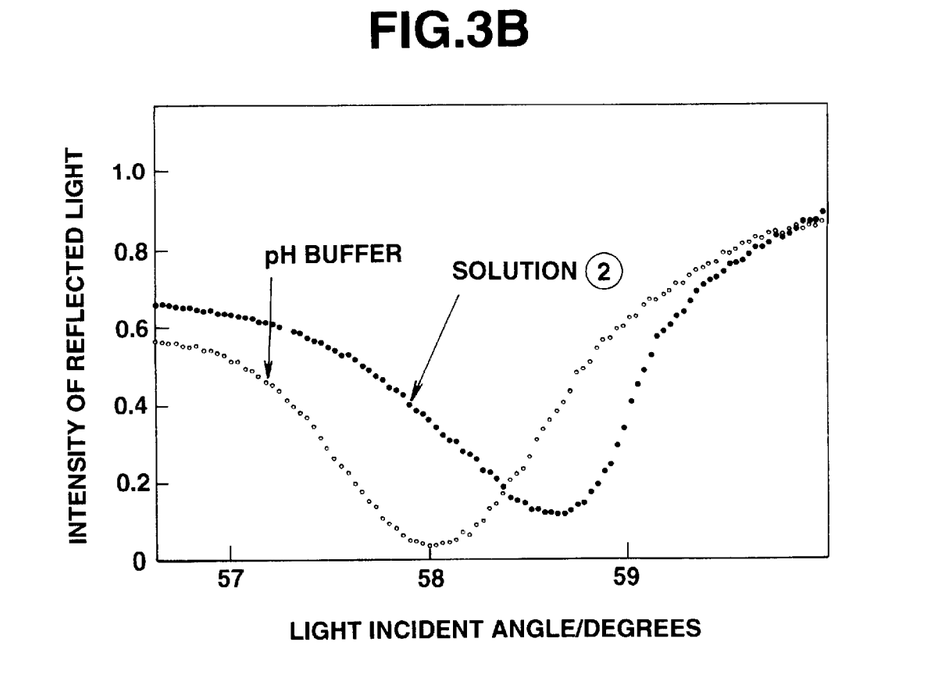
FIG. 3B is a graph illustrating resonance spectra obtained in respective cases in embodiments of the present invention.

The gold thin film 12 is divided into a plurality of strip portions each extending in the right and left directions in FIGS. 3A and 3B, and anti-HIV-1 emv gp 120/160 monoclonal antibody is carried on some strip portions of the gold thin film 12 similarly to Example 1 which illustrates the first embodiment, to form a sensitive dielectric layer. Immunoglobulin G (produced by Sigma Co.) is similarly fixed to some other strip portions of the gold thin film 12, in place of the anti-HIV-1 emv gp 120/160 monoclonal antibody.

The thus-completed sensor apparatus is dipped in 20 mM sodium phosphate buffer (pH 7.5) including 0.15 M NaCl. Light emitted from each laser and reflected by each strip portion of the gold thin film 12 is detected by each one-dimensional CCD sensor array of the two-dimensional CCD sensor array 10. Output signals are observed by a multi-channel synchroscope, and each surface plasmon resonance on each strip portion corresponding to each incident angle is measured. As a result, a resonance spectrum with a minimum at the incident angle of 62.0° was obtained for the strip portion with the anti-HIV-1 emv gp 120/160 monoclonal antibody fixed thereon. Further, a resonance spectrum with a minimum at the incident angle of 66.0° was obtained for the strip portion with the immunoglobulin G fixed thereon.

Antigen substance of recombinant HIV-1 gp 120, which is detection-object material, is dissolved in the buffer to obtain a concentration of 0.02 mg/ml. The sensor apparatus is dipped in this antigen substance solution, and the resonance spectrum is similarly measured. As a result, a resonance spectrum with a minimum at the incident angle of 64.0° was obtained for the strip portion with the anti-HIV-1 emv gp 120/160 monoclonal antibody fixed thereon. In contrast, the resonant angle remained unchanged for the strip portion with immunoglobulin G fixed thereon.

Further, anti-immunoglobulin G, which is detection-object material, is dissolved in buffer to obtain a concentration of 0.02 mg/ml. The sensor apparatus is dipped in this solution, and the resonance spectrum is similarly measured. As a result, a resonance spectrum with a minimum at the incident angle of 62.0° was obtained for the strip portion with the anti-HIV-1 emv gp 120/160 monoclonal antibody fixed thereon. This resonance spectrum is the same spectrum as for a blank. In contrast, the resonant angle was changed to 67.5° for the strip portion with the immunoglobulin G fixed thereon. It was known therefrom that the surface plasmon resonance sensor apparatus of the present invention can detect, corresponding to antigens fixed to the respective strip portions on the gold thin film 12, many components of their antibodies simultaneously and singularly.

EXAMPLE 4

A gold thin film 12 formed according to Example 3 is divided into a plurality of strip portions, and probe DNA ① is carried on some strip portions similarly to Example 2 to form a sensitive dielectric layer. Deoxyribo-thymidylic acid with polymerization degree of 25 (T25) is similarly fixed to some other strip portions of the gold thin film 12, in place of the ①.

The thus-completed sensor apparatus is dipped in 20 mM sodium phosphate buffer (pH 7.5) including 0.15 M NaCl. Light reflected from each strip portion of the gold thin film 12 is detected by each one-dimensional CCD sensor array of the two-dimensional CCD sensor array 10. Output signals are observed by the multi-channel synchroscope, and each surface plasmon resonance on each strip portion corresponding to each incident angle is measured. As a result, a resonance spectrum with a minimum at the incident angle of 58.0° was obtained for the strip portion with ① fixed thereon. A resonance spectrum with a minimum at the incident angle of 58.0° was also obtained for the strip portion with T25 fixed thereto.

The ② of Example 2 which is detection-object material, is then dissolved in buffer to obtain a concentration of 0.005 mg/ml. The sensor apparatus is dipped in this antigen substance solution, and the resonance spectrum is similarly measured. As a result, a resonance spectrum with a minimum at the incident angle of 58.7° was obtained for the strip portion with ① fixed thereon. In contrast, the resonant angle remained unchanged for the strip portion with T25 fixed thereto.

Further, deoxyribo-adenylic acid with a polymerization degree of 25 (A25), which is another detection-object material, is dissolved in buffer to obtain a solution concentration of 0.005 mg/ml. The sensor apparatus is dipped in this solution, and the resonance spectrum is similarly measured. As a result, a resonance spectrum with a minimum at the incident angle of 58.0° was obtained for the strip portion with ① fixed thereon. This resonance spectrum is the same spectrum as for a blank. In contrast, the resonant angle was changed to 59.0° for the strip portion with T25 fixed thereon. Even in such a case, it was known therefrom that the surface plasmon resonance sensor apparatus of the present invention can detect, corresponding to antigens fixed to the respective strip portions on the gold thin film 12, many components of their antibodies simultaneously and singularly.

A third preferred embodiment of the present invention is directed to a surface plasmon resonance sensor apparatus using a one-dimensional array of surface emitting lasers and a two-dimensional array of CCD sensors and capable of measuring a single component over a wide range of its concentration. The sensor structure of this embodiment is the same as illustrated in FIGS. 4A and 4B of the second embodiment.

EXAMPLE 5

A gold thin film 12 is divided into a plurality of strip portions similarly to Example 3, and anti-HIV-1 emv gp 120/160 monoclonal antibody is carried on some strip portions of the gold thin film 12 similarly to Example 1 to form a sensitive dielectric layer. Anti-HIV-1 emv gp 120/160 monoclonal antibody with a concentration of 1/100 of the above is similarly fixed to some other strip portions of the gold thin film 12.

The thus-completed sensor is dipped in 20 mM sodium phosphate buffer (pH 7.5) including 0.15 M NaCl. Light reflected by each strip portion of the gold thin film 12 is detected by each one-dimensional CCD sensor array of the two-dimensional CCD sensor array 10. Output signals are observed by the multi-channel synchroscope, and each surface plasmon resonance on each strip portion corresponding to each incident angle is measured. As a result, a resonance spectrum with a minimum at the incident angle of 62.0° was obtained for the strip portion with anti-HIV-1 emv gp 120/160 monoclonal antibody fixed thereon similarly to Example 1. A resonance spectrum with a minimum at the incident angle of 61.0° was obtained for the strip portion with the antigen of 1/100 concentration fixed thereon.

Antigen substance of recombinant HIV-1 gp 120, which is detection-object material, is then dissolved in buffer to obtain a concentration of 0.02 mg/ml. The sensor apparatus is dipped in this antigen substance solution, and the reso- nance spectrum is similarly measured. As a result, a resonance spectrum with a minimum at the incident angle of 64.0° was obtained for the strip portion with anti-HIV-1 emv gp 120/160 monoclonal antibody fixed thereon, similarly to Example 1. In contrast, the resonant angle only slightly increased for the strip portion with the antigen of 1/100 concentration fixed thereon.

Further, recombinant HIV-1 gp 120, which is detection-object material, is dissolved in buffer to obtain 0.2 mg/ml. The sensor apparatus is dipped in this solution, and the resonance spectrum is similarly measured. As a result, a resonance spectrum with a minimum at the incident angle of 62.0° was obtained for the strip portion with the antigen of 1/100 concentration fixed thereon. It was thus known therefrom that the surface plasmon resonance sensor apparatus of the present invention can detect, corresponding to antigens of various concentrations fixed to the respective strip portions on the gold thin film 12, its antibody singularly in a wide dynamic range.

EXAMPLE 6

A gold thin film 12 formed according to Example 3 is divided into a plurality of strip portions, and ① is carried on some strip portions similarly to Example 2 to form a sensitive dielectric layer. The ① with a concentration of 1/100 of the above is similarly fixed to some other strip portions of the gold thin film 12.

The sensor apparatus is dipped in 20 mM sodium phosphate buffer (pH 7.5) including 0.15 M NaCl. Light reflected by each strip portion of the gold thin film 12 is detected by each one-dimensional CCD sensor array of the two-dimensional CCD sensor array 10. Output signals are observed by the multi-channel synchroscope, and each surface plasmon resonance on each strip portion corresponding to each incident angle is measured. As a result, a resonance spectrum with a minimum at the incident angle of 58.0° was obtained for the strip portion with ① fixed thereon similarly to the second case in the first embodiment. A resonance spectrum with a minimum at the incident angle of 57.6° was obtained for the strip portion with the antigen of 1/100 concentration fixed thereon.

The ② of Example 2 which is detection-object material, is then dissolved in buffer to obtain a concentration of 0.005 mg/ml. The sensor apparatus is dipped in this antigen substance solution, and the resonance spectrum is similarly measured. As a result, a resonance spectrum with a minimum at the incident angle of 58.7° was obtained for the strip portion with ① fixed thereon similarly to the second case in the first embodiment. In contrast, the resonant angle only slightly increased for the strip portion with ① of 1/100 concentration fixed thereon.

Further, ② is dissolved in buffer to obtain a concentration of 0.005 mg/ml. The sensor apparatus is dipped in this solution, and the resonance spectrum is similarly measured. As a result, a resonance spectrum with a minimum at the incident angle of 58.1° was obtained for the strip portion with ① of 1/100 concentration fixed thereon. Even in such a case, it was known therefrom that the surface plasmon resonance sensor apparatus of the present invention can detect, corresponding to concentrations of probes fixed to the respective strip portions on the gold thin film 12, their complementary chains singularly over a wide dynamic range.

Figure 5A:
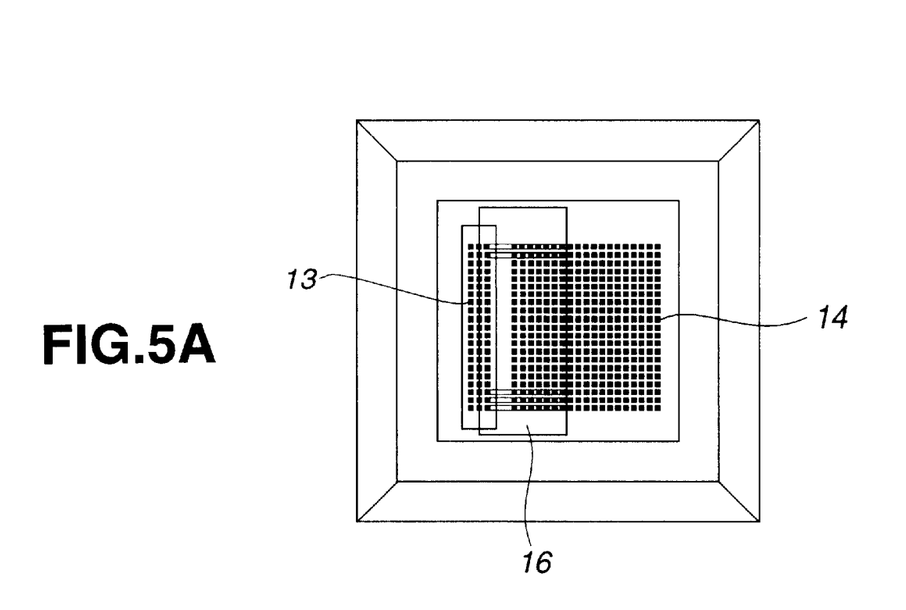
FIG. 5A is a plan view illustrating a fourth embodiment of a surface plasmon resonance sensor apparatus in which a two-dimensional array of surface emitting lasers and a two-dimensional array of CCD sensors are arranged on a common substrate.
Figure 5B:
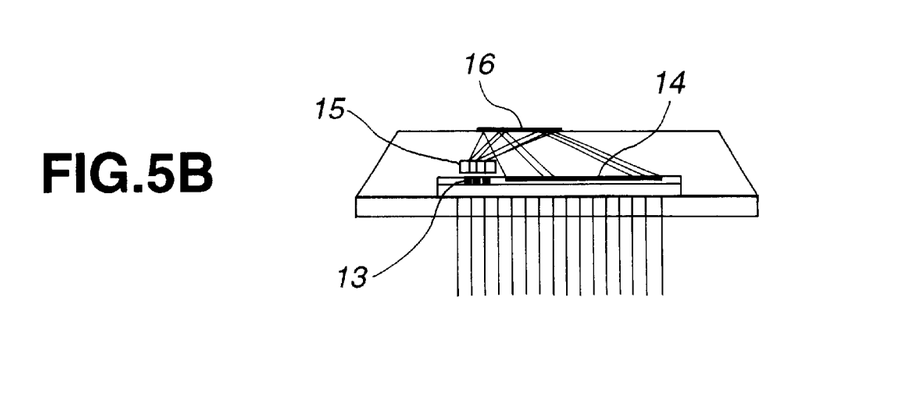
FIG. 5B is a side view illustrating the fourth embodiment of the surface plasmon resonance sensor apparatus.

A fourth preferred embodiment of the present invention is directed to a surface plasmon resonance sensor apparatus using a two-dimensional array of surface emitting lasers and a two-dimensional array of CCD sensors. Plan and side views of the sensor structure of this embodiment are illustrated in FIGS. 5A and 5B, respectively. As illustrated in FIGS. 5A and 5B, similarly to the second embodiment, the two-dimensional surface emitting laser array 13 and the two-dimensional CCD sensor array 14 are arranged on a Si substrate.

EXAMPLE 7

A cylindrical lens array 15, in which a plurality of cylindrical lenses extending in up and down directions in FIG. 4A are arranged along right and left directions in FIGS. 4A and 4B, is provided above the two-dimensional surface emitting laser array 13 to expand each laser light emitted from the laser array 13 in the arrangement direction of the two-dimensional CCD sensor array 14 (in right and left directions in FIGS. 4A and 4B). Each elongate cylindrical lens of the cylindrical lens array 15 corresponds to each one-dimensional array of the two-dimensional surface emitting laser array 13 extending along the up and down directions in FIG. 4A. Each expanded laser light is totally reflected by the surface of light-transmitting resin on which a metal thin film 16 is formed. The focal length of each cylindrical lens of the cylindrical lens array 15 is decided such that the intensity of each totally-reflected light can be measured by the CCD sensor array 14 corresponding to its incident angle.

As the metal thin film 16, gold is deposited with a thickness of 500 Å on the surface of the light-transmitting resin, similarly to Example 3.

The gold thin film 16 is divided into a plurality of strip portions extending in the right and left directions in FIGS. 4A and 4B. Anti-HIV-1 emv gp 120/160 monoclonal antibody is carried on some strip portions of the gold thin film 16 similarly to Example 3. Immunoglobulin G is further carried on some other strip portions of the gold thin film 16 similarly to Example 3.

Furthermore, protein is fixed to some other strip portions of the gold thin film 16 in the following manner.

(1) Dithio-bis-propionic acid succinimide is dissolved in deoxidized acetone to obtain a concentration of 0.01 mM.

(2) The strips of the gold thin film 16 are dipped in this solution to fix succinimide to the gold thin film 16 by employing the phenomenon that disulfide self-organizes on the gold surface.

(3) Bovine serum albumin (produced by Sigma Co.) is then dissolved in 20 mM sodium phosphate buffer (pH 7.5) to obtain a 1% concentration. The gold strips are dipped in this solution for an hour to fix albumin to the gold thin film 16.

The thus-completed sensor apparatus is dipped in 20 mM sodium phosphate buffer (pH 7.5) including 0.15 M NaCl. Light reflected by each strip portion of the gold thin film 16 is detected by each one-dimensional CCD sensor array of the two-dimensional CCD sensor array 14 extending in the right and left directions in FIGS. 4A and 4B. Output signals are observed by the multi-channel synchroscope, and each surface plasmon resonance on each strip portion corresponding to each incident angle is measured. As a result, the same responses as those in Example 3 were observed on the strip portion with the anti-HIV-1 emv gp 120/160 monoclonal antibody fixed thereon and on the strip portion with the immunoglobulin G fixed thereon.

Protein bonded to fatty acid (see B. Specht et. al, J. Biotechnol., 33 (1994) 259–269), which is detection-object material, is then dissolved in buffer to obtain a concentration of 0.02 mg/ml. The sensor apparatus is dipped in this solution, and the resonance spectrum is similarly measured. As a result, a change of the resonant angle was observed neither on the strip portion with the anti-HIV-1 emv gp 120/160 monoclonal antibody fixed thereon nor on the strip portion with the immunoglobulin G fixed thereon. In contrast, the resonant angle was changed from 43.0° to 44.5° on the strip portion with the bovine serum albumin fixed thereon. Thus, it was known therefrom that singular response occurred on each strip portion for the detection object.

Further, on the strip portion with the bovine serum albumin fixed thereon, the surface plasmon resonance occurred at an angle larger than the incident angle measurable in the second embodiment. It was thus known therefrom that a spectrum over a wide incident-angle range could be measured by using the arrayed surface emitting lasers and the interaction with substance fixed to the metal thin film could be widely sensed.

EXAMPLE 8

A gold thin film 16 as in Example 7 is divided into a plurality of strip portions, and ① of Example 2 is carried on some strip portions. Further, deoxyribo-thymidylic acid with polymerization degree of 25 (T25) is fixed to some other strip portions of the gold thin film 16, similarly to Example 4, and oligo-deoxy-nucleotide (AGCT) of a polymerization degree of 20 having a repetitive arrangement of ACGT is fixed to some other strip portions.

The sensor apparatus is dipped in 20 mM sodium phosphate buffer (pH 7.5) including 0.15 M NaCl. Light reflected by each strip portion of the gold thin film 16 is detected by the two-dimensional CCD sensor array 14. Output signals are observed by the multi-channel synchroscope, and each surface plasmon resonance on each strip portion corresponding to each incident angle is measured. As a result, the same responses as those in Example 4 were observed on the respective strip portions, including the strip portion of (AGCT).

Single-chain DNA of M13mp18ss, whose molar weight is large compared with that of detection-object material in Examples 2, 4 and 6, is then dissolved to obtain a concentration of 0.02 mg/ml. The sensor apparatus is dipped in this solution, and the resonance spectrum is similarly measured. As a result, a change of the resonant angle was observed neither for the strip portion of T25 nor the strip of (AGCT). In contrast, the resonant angle was changed from 58.0° to 61.5° for the strip portion with ① fixed thereon. It was thus known therefrom that singular response occurred on each strip portion for the detection object.

Further, on the strip portion with ① fixed thereon, the surface plasmon resonance occurred at an angle larger than the incident angle measurable in the second embodiment. Even in this case, it was thus known therefrom that a spectrum over a wide incident-angle range could be measured by using the arrayed surface emitting lasers and the interaction with substance fixed to the metal thin film could be widely sensed.

As described in the foregoing, according to the surface plasmon resonance sensor apparatus using a surface emitting laser of the present invention, necessary optical elements are all arranged on a common chip, so that small-sizing of the sensor apparatus, relatively low cost, and high productivity can be achieved. Further, the sensor apparatus applicable to many-component sensing, and sensing over a wide concentration-range can be achieved by using features of the surface emitting laser.

Except as otherwise disclosed herein, the various components shown in outline or block form in the Figures are individually well known in the laser device and sensors, and their internal construction and operation are not critical either to the making or using of this invention or to a description of the best mode of the invention.

While the present invention has been described with respect to what is presently considered to be the preferred embodiments, it is to be understood that the invention is not limited to the disclosed embodiments. The present invention is intended to cover various modifications and equivalent arrangements included within the spirit and scope of the appended claims.

What is claimed is:

1. A surface plasmon resonance sensor apparatus comprising:
   (a) a common substrate;
   (b) a sensor array arranged in a predetermined direction and spaced on said common substrate;
   (c) a light-transmitting medium spaced above said common substrate;
   (d) a metal thin film formed on said light-transmitting medium;
   (e) a surface emitting laser spaced on said common substrate adapted to emit light through said light-transmitting medium to be reflected from said metal thin film and simultaneously generate a surface plasmon resonance sufficient to change intensity of light reflected from said metal thin film such that light emitted from said surface emitting laser is polarized in said predetermined direction without use of a polarizer, wherein the light emission point of the surface-emitting laser is elliptically shaped; and
   (f) an optical element positioned between said surface emitting laser and said metal thin film for spreading the light emitted from said surface emitting laser in said predetermined direction; wherein said surface emitting laser, said metal thin film and said sensor array are positioned to measure the intensity of the light reflected by said metal thin film.

2. A surface plasmon resonance sensor apparatus according to claim 1, wherein a sensitive dielectric layer is provided on said metal thin film on a side opposite to said light-transmitting medium.

3. A surface plasmon resonance sensor apparatus according to claim 2, wherein said sensitive dielectric layer contains a substance fixed thereon, said substance selected from the group consisting of antigen, antibody, hormone, receptor, polypeptide, nucleic acid, cell, cell membrane, glycoprotein, lipid and pigment.

4. A surface plasmon resonance sensor apparatus according to claim 2, wherein said sensitive dielectric layer contains substance fixed thereon, said substance being a probe nucleic acid.

5. A surface plasmon resonance sensor apparatus according to claim 4, wherein said sensitive dielectric layer comprises a layer capable of interacting with a target nucleic acid contained in a sample and changing a physicochemical property thereof.

6. A surface plasmon resonance sensor apparatus according to claim 5, wherein the probe nucleic acid contains a portion of a base arrangement of the target nucleic acid replaced by a complementary base arrangement.

7. A surface plasmon resonance sensor apparatus according to claim 6, wherein the probe nucleic acid is capable of interacting with a target nucleic acid of DNA, cDNA, or RNA.

8. A surface plasmon resonance sensor apparatus according to claim 7, wherein the RNA target nucleic acid is mRNA, tRNA, or rRNA.

9. A surface plasmon resonance sensor apparatus according to claim 6, wherein said probe nucleic acid is DNA, cDNA, or RNA.

10. A surface plasmon resonance sensor apparatus according to claim 9, wherein said probe nucleic acid RNA is mRNA, tRNA, or rRNA.

11. A surface plasmon resonance sensor apparatus according to claim 6, wherein said probe nucleic acid is protein nucleic acid.

12. A surface plasmon resonance sensor apparatus according to claim 6, wherein the target nucleic acid is protein nucleic acid.

13. A surface plasmon resonance sensor apparatus according to claim 2, wherein said sensitive dielectric layer comprises a layer capable of interacting with a sample contained in a gas or liquid and changing a physicochemical property thereof.

14. A surface plasmon resonance sensor apparatus according to claim 1, wherein said optical element is a lens.

15. A surface plasmon resonance sensor apparatus according to claim 1, wherein said optical element is a hologram device.

16. A surface plasmon resonance sensor apparatus according to claim 1, wherein said surface emitting laser is a single surface emitting laser, and said sensor array is a one-dimensional array of sensors for measuring surface plasmon resonant light of the light emitted from said single surface emitting laser.

17. A surface plasmon resonance sensor apparatus according to claim 1, wherein said surface emitting laser is a one-dimensional array of surface emitting lasers, and said sensor array is a two-dimensional array of sensors, each one-dimensional sensor array of said two-dimensional array of sensors measuring surface plasmon resonant light of each light emitted from each surface emitting laser of said one-dimensional array of surface emitting lasers.

18. A surface plasmon resonance sensor apparatus according to claim 1, wherein said surface emitting laser is a two-dimensional array of surface emitting lasers, and said sensor array,is a two-dimensional array of sensors, each one-dimensional sensor array of said two-dimensional array of sensors measuring surface plasmon resonant light of light emitted from each one-dimensional surface emitting laser array of said two-dimensional array of surface emitting lasers.

19. A surface plasmon resonance sensor apparatus according to claim 1, wherein said common substrate is a silicon substrate.

20. A surface plasmon resonance sensor apparatus according to claim 1, wherein said light-transmitting medium is glass or plastic.

21. A surface plasmon resonance sensor apparatus according to claim 1, wherein said metal thin film is gold, silver, copper, zinc, aluminum, or potassium.

22. A surface plasmon resonance sensor apparatus according to claim 1, wherein said sensor array is an array of carged-coupled devices.

23. A surface plasmon resonance sensor apparatus according to claim 1, wherein said surface emitting laser comprises a plurality of surface emitting lasers.

24. A surface plasmon resonance sensor apparatus according to claim 1, wherein said surface emitting laser comprises a one-dimensional array of surface emitting lasers.

25. A surface plasmon resonance sensor apparatus according to claim 1, wherein said surface emitting laser comprises a two-dimensional array of surface emitting lasers.

* * * * *

UNITED STATES PATENT AND TRADEMARK OFFICE
CERTIFICATE OF CORRECTION

PATENT NO.    : 6,424,418 B2
DATED         : July 23, 2002
INVENTOR(S)   : Yuji Kawabata et al.

It is certified that error appears in the above-identified patent and that said Letters Patent is hereby corrected as shown below:

Column 4,
Line 27, "influeneces" should read -- influences --.

Column 5,
Line 23, "is" should be deleted.

Column 8,
Line 18, "an" should read -- a --.

Column 17,
Line 53, "substance" (first occurrence) should read -- a substance --.

Column 18,
Line 40, "array,is" should read -- array is --; and
Line 56, "carged-coupled" should read -- charge-coupled --.

Signed and Sealed this

Twenty-eighth Day of January, 2003

JAMES E. ROGAN
*Director of the United States Patent and Trademark Office*